(12) United States Patent
Young et al.

(10) Patent No.: US 7,101,853 B2
(45) Date of Patent: Sep. 5, 2006

(54) METHOD FOR TREATING OR PREVENTING GASTRITIS USING AMYLIN OR AMYLIN AGONISTS

(75) Inventors: Andrew A. Young, San Diego, CA (US); Bronislava Gedulin, San Diego, CA (US); Gareth Wyn Beynon, Brightwell-cum Sotwell (GB)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 08/851,965

(22) Filed: May 6, 1997

(65) Prior Publication Data

US 2002/0010133 A1 Jan. 24, 2002

(51) Int. Cl.
*A61K 38/00* (2006.01)

(52) U.S. Cl. .............................. 514/14; 514/12; 514/13
(58) Field of Classification Search .............. 514/12–14
See application file for complete search history.

(56) References Cited

U.S. PATENT DOCUMENTS

| 5,686,411 A | 11/1997 | Gaeta et al. |
| 5,795,861 A | 8/1998 | Kolterman et al. |
| 6,114,304 A | 9/2000 | Kolterman et al. |

FOREIGN PATENT DOCUMENTS

WO  WO 95/07098 A1  3/1995

OTHER PUBLICATIONS

Beaumont, et al., "High Affinity Amylin Binding Sites in Rat Brain," *Molecular Pharmacology*, 44:493–497 (1993).
Gray, et al., "A Role for Calcitonin Gene–Related Peptide in Protection Against Gastric Ulceration," *Annals of Surgery*, 219(1):58–64 (1994)—Abstract.
Hartter, et al., "Basal and Stimulated Plasma Levels of Pancreatic Amylin Indicate its Co–secretion with Insulin in Humans," *Diabetologia*, 34:52–54 (1991).
Maggi, et al., "Anti–ulcer Activity of Calcitonin Gene–Related Peptide in Rats," *Gen. Pharmacol.*, 18(1):33–34 (1987)—Abstract.
Miller, et al., "Calcitonin Gene–Related Peptide (CGRP) Upregulates the Restitution of Rat Gastric Mucosa In Vitro," *Journal of Surgical Research*, 58(4):421–424 (1995)—Abstract.

Pittner, "Lack of Effect of Calcitonin Gene–Related Peptide and Amylin on Major Markers of Glucose Metabolism in Hepatocytes," *European Journal of Pharmacology*, 325:189–197 (1997).
Tache, "Inhibition of Gastric Acid Secretion and Ulcers and by Calciton Gene–Related Peptide," *Ann. N.Y. Acad. Sci.*, 657:240–247 (1992).
Young, et al., "Preclinical Pharmacology of Pramlintide in the Rat: Comparisons With Human and Rat Amylin," *Drug Development Research*, 37:231–248 (1996).
Young, et al., "$^{8-37}$hCGRP, an Amylin Receptor Antagonist, Enhances the Insulin Response and Perturbs the Glucose Response to Infused Arginine in Anesthetized Rats," *Molecular and Cellular Endocrinology*, 84:R1–R5 (1992).
Guidobono, et al., "Effect of amylin on gastric acid secretion and gastric ulcers in the rat," *Fund. Clinical & Pharm.*, Abstract 3rd joint meeting of the Societa Italiana di Farmacologia and the Association Francaise des Pharmacologistes; Capri, Italy May 23–26, 1996.
Database WPI, Section Ch, Week 199546, Derwent Publications Ltd., London, GB; AN 1995–351860 XP002163755 (1994).
Gedulin, et al., "Amylin inhibits pentagastrin–simulated gastric acid secretion and protects against ethanol–induced gastric mucosal damage in rats," *Diabetologia*, 40(Supp 1): Jun. 1997.
Kolterman et al., "Effect of 14 Days' Subcutaneous Administration of the Human Amylin Analogue, Pramlintide (AC137), on an Intravenous Insulin Challenge and Response to a Standard Liquid Meal in Patients with IDDM," *Diabetologia*, 39:492–499 (1996).

*Primary Examiner*—Bennett Celsa
(74) *Attorney, Agent, or Firm*—Arnold & Porter LLP

(57) ABSTRACT

Methods for treating or preventing gastritis or gastric injury are disclosed, comprising administering a therapeutically effective amount of an amylin or an amylin agonist. Methods are also disclosed for the treatment of pain, fever, inflammation, arthritis, hypercoagulability, or other conditions for which a non-steroidal anti-inflammatory drug would be indicated, comprising administering an amylin or amylin agonist in conjunction with administering a therapeutically effective amount of a non-steroidal anti-inflammatory agent. Pharmaceutical compositions comprising an amylin or amylin agonist and a non-steroidal anti-inflammatory drug are also disclosed.

26 Claims, 1 Drawing Sheet

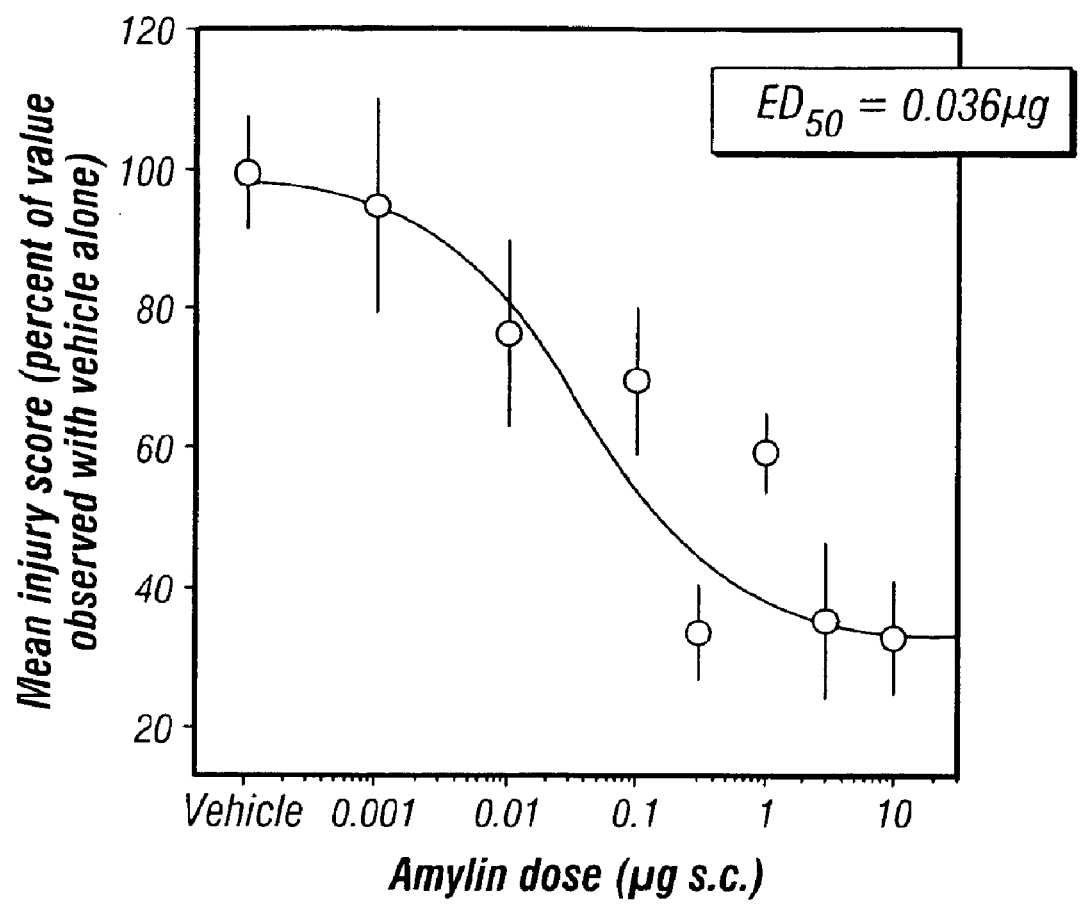

METHOD FOR TREATING OR PREVENTING GASTRITIS USING AMYLIN OR AMYLIN AGONISTS

FIELD OF THE INVENTION

The present invention relates to methods for treating or preventing gastritis or gastric injury by administering an amylin or an amylin agonist. The present invention also relates to the treatment of pain, fever, inflammation, arthritis, hypercoagulability, or other conditions for which a non-steroidal anti-inflammatory drug would be indicated, comprising administering an amylin or an amylin agonist in conjunction with a non-steroidal anti-inflammatory drug. Pharmaceutical compositions comprising an amylin or an amylin agonist and a non-steroidal anti-inflammatory agent are also described by the present invention.

BACKGROUND

Publications and other materials including patents and patent applications used to illuminate the specification are hereby incorporated by reference.

Amylin

The structure and biology of amylin have previously been reviewed. See, for example, Rink et al., *Trends in Pharmaceutical Sciences,* 14:113–118 (1993); Gaeta and Rink, *Med. Chem. Res.,* 3:483–490 (1994); and, Pittner et al., *J. Cell. Biochem.,* 55S:19–28 (1994).

Amylin is a 37 amino acid protein hormone. It was isolated, purified and chemically characterized as the major component of amyloid deposits in the islets of pancreases of human Type II diabetics (Cooper et al., *Proc. Natl. Acad. Sci., USA* 84:8628–8632 (1987)). The amylin molecule has two important post-translational modifications: the C-terminus is amidated, and the cysteines in positions 2 and 7 are cross-linked to form an N-terminal loop. The sequence of the open reading frame of the human amylin gene shows the presence of the Lys-Arg dibasic amino acid proteolytic cleavage signal, prior to the N-terminal codon for Lys, and the Gly prior to the Lys-Arg proteolytic signal at the C-terminal position, a typical sequence for amidation for protein amidating enzyme, PAM (Cooper et al., *Biochm. Biophys. Acta,* 1014:247–258 (1989)). Amylin is the subject of United Kingdom patent application Ser. No. 8709871, filed Apr. 27, 1987, and corresponding U.S. Pat. No. 5,367,052, issued Nov. 22, 1994.

In Type 1 diabetes, amylin has been shown to be deficient, and combined replacement with insulin has been proposed as a preferred treatment over insulin alone in all forms of diabetes. The use of amylin and other amylin agonists for the treatment of diabetes mellitus is the subject of U.S. Pat. No. 5,175,145, issued Dec. 29, 1992. Pharmaceutical compositions containing amylin and amylin plus insulin are described in U.S. Pat. No. 5,124,314, issued Jun. 23, 1992.

Amylin is primarily synthesized in pancreatic beta cells and is secreted in response to nutrient stimuli such as glucose and arginine. Studies with cloned beta-cell tumor lines (Moore et al., *Biochem. Biophys. Res. Commun.,* 179(1) (1991)), isolated islets (Kanatsuka et al., *FEBS Letts.,* 259(1), 199–201 (1989)) and perfused rat pancreases (Ogawa et al., *J. Clin. Invest.,* 85:973–976 (1990)) have shown that short pulses, 10 to 20 minutes, of nutrient secretagogues such as glucose and arginine, stimulate release of amylin as well as insulin. The molar amylin:insulin ratio of the secreted proteins varies between preparations from about 0.01 to 0.4, but appears not to vary much with acute stimuli in any one preparation. However, during prolonged stimulation by elevated glucose, the amylin:insulin ratio can progressively increase (Gedulin et al., *Biochem. Biophys. Res. Commun.,* 180(1):782–789 (1991)). Thus, amylin and insulin are not always secreted in a constant ratio.

It has been discovered and reported that certain actions of amylin are similar to non-metabolic actions of CGRP and calcitonin; however, the metabolic actions of amylin discovered during investigations of this recently identified protein appear to reflect its primary biologic role. At least some of these metabolic actions are mimicked by CGRP, albeit at doses which are markedly vasodilatory (see, e.g., Leighton et al., *Nature,* 335:632–635 (1988)); Molina et al., *Diabetes,* 39:260–265 (1990)).

The first discovered action of amylin was the reduction of insulin-stimulated incorporation of glucose into glycogen in rat skeletal muscle (Leighton et al., *Nature,* 335:632–635 (1988)); the muscle was made "insulin-resistant." Subsequent work with rat soleus muscle ex-vivo and in vitro has indicated that amylin reduces glycogen synthase activity, promotes conversion of glycogen phosphorylase from the inactive b form to the active a form, promotes net loss of glycogen (in the presence or absence of insulin), increases glucose-6-phosphate levels, and can increase lactate output (see, e.g., Deems et al., *Biochem. Biophys. Res. Commun.,* 181(l):116–120 (1991)); Young et al., *FEBS Letts,* 281(1,2):149–151 (1991)). Amylin appears not to affect glucose transport per se (e.g., Pittner et al., *FEBS Letts.,* 365(1):98–100 (1995)). Studies of amylin and insulin dose-response relations show that amylin acts as a noncompetitive or functional antagonist of insulin in skeletal muscle (Young et al., *Am. J. Physiol.,* 263(2):E274–E281 (1992)). There is no evidence that amylin interferes with insulin binding to its receptors, or the subsequent activation of insulin receptor tyrosine kinase (Follett et al., *Clinical Research,* 39(1):39A (1991)); Koopmans et al., *Diabetologia,* 34:218–224 (1991)).

It is believed that amylin acts through receptors present in plasma membranes. Studies of amylin and CGRP, and the effect of selective antagonists, suggest that amylin acts via its own receptor (Beaumont et al., *Br. J. Pharmacol.,* 115 (5):713–715 (1995); Wang et al., *FEBS Letts.,* 219:195–198 (1991 b)), counter to the conclusion of other workers that amylin may act primarily at CGRP receptors (e.g., Chantry et al., *Biochem. J.,* 277:139–143 (1991)); Galeazza et al., *Peptides,* 12:585–591 (1991)); Zhu et al., *Biochem. Biophys. Res. Commun.,* 177(2):771–776 (1991)). Amylin receptors and their use in methods for screening and assaying for amylin agonist and antagonist compounds are described in U.S. Pat. No. 5,264,372, issued Nov. 23, 1993.

While amylin has marked effects on hepatic fuel metabolism in vivo, there is no general agreement as to what amylin actions are seen in isolated hepatocytes or perfused liver. The available data do not support the idea that amylin promotes hepatic glycogenolysis, i.e., it does not act like glucagon (e.g., Stephens et al., *Diabetes,* 40:395–400 (1991); Gomez-Foix et al., *Biochem J.,* 276:607–610 (1991)). It has been suggested that amylin may act on the liver to promote conversion of lactate to glycogen and to enhance the amount of glucose able to be liberated by glucagon (see Roden et al., *Diabetologia,* 35:116–120 (1992)). It is most likely that amylin has no direct effect on liver cells. (Pittner, R. A., *Eur. J. of Pharm.* (1997) (in press)).

In fat cells, contrary to its action in muscle, amylin has no detectable actions on insulin-stimulated glucose uptake, incorporation of glucose into triglyceride, $CO_2$ production (Cooper et al., *Proc. Natl. Acad. Sci.*, 85:7763–7766 (1988)), epinephrine-stimulated lipolysis, or insulin-inhibition of lipolysis (Lupien and Young, "Diabetes Nutrition and Metabolism—Clinical and Experimental," Vol. 6(1), pages 1318 (February 1993)). Amylin thus exerts tissue-specific effects, with direct action on skeletal muscle, and indirect (via supply of substrate) effects on liver, while adipocytes appear "blind" to the presence or absence of amylin.

It has also been reported that amylin can have marked effects on secretion of insulin. In isolated islets (Ohsawa et al., *Biochem. Biophys. Res. Commun.*, 160(2):961–967 (1989)), in the perfused pancreas (Silvestre et al., *Reg. Pept.*, 31:23–31 (1990)), and in the intact rat (Young et al., *Mol. Cell. Endocrinol.*, 84:R1–R5 (1992)), some experiments indicate that amylin inhibits insulin secretion. Other workers, however, have been unable to detect effects of amylin on isolated β-cells, on isolated islets, or in the whole animal (see Broderick et al., *Biochem. Biophys. Res. Commun.* 177:932–938 (1991) and references therein).

Amylin or amylin agonists potently inhibit gastric emptying in rats (Young et al., *Diabetologia*, 38(6):642–648 (1995)), dogs (Brown et al., *Diabetes*, 43(Suppl 1):172A (1994)) and humans (Macdonald et al., *Diabetologia*, 38 (Suppl 1):A32 (abstract 118) (1995)). Gastric emptying is reportedly accelerated in amylin-deficient type 1 diabetic BB rats (Young et al., *Diabetologia*, supra; Nowak et al., *J. Lab. Clin. Med.*, 123(1):110–6 (1994)) and in rats treated with the selective amylin antagonist, AC187 (Gedulin et al., *Diabetologia*, 38 (Suppl 1):A244 (1995)). Methods for reducing gastric motility and slowing gastric emptying comprising the administration of an amylin agonist (including amylin) are the subject of U.S. patent application Ser. No. 08/118,381, filed Sep. 7, 1993, and U.S. patent application Ser. No. 08/302,069, filed Sep. 7, 1994 (and corresponding PCT application, Publication No. WO 95/07098, published Mar. 16, 1995). The effect of amylin on gastric emptying appears to be physiological (operative at concentrations that normally circulate). Suprapyhsiological levels of amylin have also been studied with regard to the inhibition of gastric acid secretion (Guidobono, F., et al., *Peptides*, 15:699–702 (1994) and in regard to protection from gastritis. (Guidobono et al., *Brit. J. Pharm.*, 120:581–86 (1997)). The latter authors reported that subcutaneous injections of amylin had no effect on ethanol- or indomethacin-induced gastritis in rats, although intracerebroventricular injections did have an effect. The same authors also concluded that any gastroprotective effects of amylin were distinct from effects to inhibit acid secretion.

Non-metabolic actions of amylin include vasodilator effects which may be mediated by interaction with CGRP vascular receptors. Reported in vivo tests suggest that amylin is at least about 100 to 1000 times less potent than CGRP as a vasodilator (Brain et al., *Eur. J. Pharmacol.*, 183:2221 (1990); Wang et al., *FEBS Letts.*, 291:195–198 (1991)). The effect of amylin on regional hemodynamic actions, including renal blood flow, in conscious rats has been reported (Gardiner et al., *Diabetes*, 40:948–951 (1991)). The authors noted that infusion of rat amylin was associated with greater renal vasodilation and less mesenteric vasoconstriction than is seen with infusion of human α-CGRP. They concluded that, by promoting renal hyperemia to a greater extent than did α-CGRP, rat amylin could cause less marked stimulation of the renin-angiotensin system, and thus, less secondary angiotensin II-mediated vasoconstriction. It was also noted, however, that during coninfusion of human α-$^{8-37}$CGRP and rat amylin, renal and mesenteric vasoconstrictions were unmasked, presumably due to unopposed vasoconstrictor effects of angiotensin II, and that this finding is similar to that seen during coinfusion of human A-CGRP and human α-$^{8-37}$CGRP (id. at 951).

Injected into the brain, or administered peripherally, amylin has been reported to suppress food intake, e.g., Chance et al., *Brain Res.*, 539:352–354 (1991)), an action shared with CGRP and calcitonin. The effective concentrations at the cells that mediate this action are not known. Amylin has also been reported to have effects both on isolated osteoclasts where it caused cell quiescence, and in vivo where it was reported to lower plasma calcium by up to 20% in rats, in rabbits, and in humans with Paget's disease (see, e.g., Zaidi et al., *Trends in Endocrinol. and Metab.*, 4:255–259 (1993)). From the available data, amylin seems to be less potent than human calcitonin for these actions. Interestingly, it was reported that amylin appeared to increase osteoclast cAMP production but not to increase cytosolic $Ca^{2+}$, while calcitonin does both (Alam et al., *Biochem. Biophys. Res. Commun.*, 179(1):134–139 (1991)). It was suggested, though not established, that calcitonin may act via two receptor types and that amylin may interact with one of these.

It has also been discovered that, surprisingly in view of its previously described renal vasodilator and other properties, amylin markedly increases plasma renin activity in intact rats when given subcutaneously in a manner that avoids any disturbance of blood pressure. This latter point is important because lowered blood pressure is a strong stimulus to renin release. Amylin antagonists, such as amylin receptor antagonists, including those selective for amylin receptors compared to CGRP and/or calcitonin receptors, can be used to block the amylin-evoked rise of plasma renin activity. The use of amylin antagonists to treat renin-related disorders is described in U.S. Pat. No. 5,376,638, issued Dec. 27, 1994.

It has also been found that amylin and amylin agonists have an analgesic effect; methods for treating pain comprising the administration of an amylin or an amylin agonist with or without a narcotic analgesic are described in U.S. application Ser. No. 08/767,169, filed Dec. 16, 1996.

In normal humans, fasting amylin levels from 1 to 10 pM and post-prandial or post-glucose levels of 5 to 20 pM have been reported (e.g., Hartter et al., *Diabetologia*, 34:52–54 (1991); Sanke et al., *Diabetologia*, 34:129–132 (1991); Koda et al., *The Lancet*, 339:1179–1180 (1992)). In obese, insulin-resistant individuals, post-food amylin levels can go higher, reaching up to about 50 pM. For comparison, the values for fasting and post-prandial insulin are 20 to 50 pM, and 100 to 300 pM respectively in healthy people, with perhaps 3-to 4-fold higher levels in insulin-resistant people. In Type 1 diabetes, where beta cells are destroyed, amylin levels are at or below the levels of detection and do not rise in response to glucose (Koda et al., *The Lancet*, 339:1179–1180 (1992)). In normal mice and rats, basal amylin levels have been reported from 30 to 100 pM, while values up to 600 pM have been measured in certain insulin-resistant, diabetic strains of rodents (e.g., Huang et al., *Hypertension*, 19:I-101-I-109 (1991); Gill et al., *Life Sciences*, 48:703–710 (1991)).

Non-Steroidal Anti-Inflammatory Drugs

Non-steroidal anti-inflammatory drugs or agents (NSAIDS) are useful analgesics, however, they have the adverse property of inducing various gastric effects in a large fraction of patients; such gastric effects include gastritis, gastric ulcer, epigastric distress, nausea, vomiting, and hemorrhage. (Woodbury, D. M. and Fingl, E. *Analgesic-antipyretics, anti-inflammatory agents, and drugs employed in the therapy of gout*, in The Pharmacological Basis of Therapeutics (Goodman, L. S., and Gilman, A., eds.) 325–43

(1975)). Such NSAIDS include salicylate, phenylbutazone, indomethacin, acetominophan, phenacetin, naproxen, and ibuprofen. This side effect is particularly a problem in patients that must continually ingest NSAIDs, such as in patients with chronic inflammatory conditions, such as rheumatoid arthritis.

SUMMARY OF THE INVENTION

We have discovered that, unexpectedly, amylins and amylin agonists have gastroprotective properties and can prevent the induction of gastritis, and thus treat or prevent gastric injury, such as gastric ulcers, when administered to a subject. The term "amylin" is understood to include compounds such as those defined by Young and Cooper in U.S. Pat. No. 5,234,906, issued Aug. 10, 1993 for "Hyperglycemic Compositions," the contents of which are hereby incorporated by this reference. For example, the term includes human amylin and species variations of it, referred to as amylin and secreted from the beta cells of the pancreas. "Amylin agonist" is also a term known in the art. The term refers to compounds which mimic effects of amylin. Amylin agonists include "amylin agonist analogues" which are derivatives of amylin which act as amylin agonists. Amylin agonists may act by binding to or otherwise directly or indirectly interacting with an amylin receptor or other receptor with which amylin itself may interact to elicit biological effects of amylin. In addition to those amylin agonists described herein, other useful amylin agonists are identified in U.S. patent application Ser. No. 08/477,849, filed May 30, 1995 and corresponding PCT application Publication No. WO 93/10146, published May 27, 1993, the disclosures of which are hereby incorporated by this reference.

Thus, in a first aspect of the invention, a method is provided for treating or preventing gastritis or gastric ulceration in a subject, comprising administering to said subject a therapeutically effective amount of an amylin or an amylin agonist, wherein said amylin agonist is not a calcitonin. In one embodiment, said gastritis or gastric ulceration is associated with the administration of a non-steroidal anti-inflammatory drug.

In the methods of the present invention, the analgesic properties of amylins and amylin agonists will supplement and augment the analgesic properties of NSAIDS, while the gastroprotective effects of amylins and amylin agonists will reduce the propensity of NSAIDS to cause gastritis and ulceration, whether the NSAIDS are being used to treat pain, or for any other purpose.

Thus, in another aspect of the invention, a method is provided for treating or preventing pain, inflammation, fever, arthritis, hypercoagulability, or other conditions for which an NSAID would be indicated comprising administering to a subject a therapeutically effective amount of an amylin or an amylin agonist, wherein said amylin agonist is not a calcitonin, and a therapeutically effective amount of a non-steroidal anti-inflammatory agent. In another preferred aspect, the invention provides a method of enhancing the analgesic activity of an NSAID in a subject, comprising administering an amylin or an amylin agonist along with said NSAID, wherein said amylin agonist is not a calcitonin. Preferably, said non-steroidal anti-inflammatory agent is selected from the group consisting of salicylate, acetominophen, phenacetin, naproxen, phenylbutazone, indomethacin, and ibuprofen.

According to the methods of the present invention, the preferred method of administration of said amylin or amylin agonist is not through intramuscular or subcutaneous injection. Most preferably, the amylin or amylin agonist is administered by a route selected from the group consisting of nasal, pulmonary, transdermal, oral, and buccal administration.

The subject may be any animal, preferably a mammal, and more preferably a human.

In other aspects of the present invention, a pharmaceutical composition is provided comprising (1) an amylin or an amylin agonist or a pharmaceutically acceptable salt thereof, wherein said amylin agonist is not a calcitonin, and (2) a non-steroidal anti-inflammatory agent in a pharmaceutically acceptable carrier and dose.

Preferably, said non-steroidal anti-inflammatory agent is selected from the group consisting of salicylate, phenacetin, naproxen, phenylbutazone, indomethacin, and ibuprofen.

In preferred embodiments of the present invention, the amylin agonist is $^{25,28,29}$Pro-h-amylin [SEQ. ID. NO.1].

Administration of an amylin or an amylin agonist may be by various routes, including subcutaneously, or intramuscularly, or through non-injectable routes of parenteral administration, such as through oral, nasal, pulmonary, transdermal, or buccal routes. Such non-injectable routes of parenteral administration are preferred because of the high potency of the amylin or amylin agonist. Oral administration is especially preferred for orally-active amylin agonists.

BRIEF DESCRIPTION OF THE DRAWINGS

The invention will be further described with reference to the accompanying drawing in which:

FIG. 1 shows the effect of subcutaneous doses of rat amylin to reduce the gastric injury induced by gavage of ethanol into rats.

DETAILED DESCRIPTION OF THE INVENTION

Amylin agonists may be identified by activity in the gastroprotection assays described below. These compounds may also be assessed by receptor binding and gastric emptying assays described below.

The nomenclature of various amylin agonist compounds useful in the present invention can be used to indicate both the peptide that the sequence is based on and the modifications made to any basic peptide amylin sequence, such as human amylin. An amino acid preceded by a superscript number indicates that the named amino acid replaces the amino acid normally present at the amino acid position of the superscript in the basic amino acid sequence. For example, "$^{18}$Arg$^{25,28}$Pro-h-amylin" refers to a peptide based on the sequence of "h-amylin" or "human-amylin" having the following substitutions: Arg replacing His at residue 18, Pro replacing Ala at residue 25 and Pro replacing Ser at residue 28. The term "des-$^1$Lys-h-amylin" refers to a peptide based on the sequence of human amylin, with the first, or N-terminal, amino acid deleted.

Amylin agonists include the following amylin agonist analogues:

i) An agonist analogue of amylin having the amino acid sequence (SEQ. ID. NO: 36):

iv) An agonist analogue of amylin having the amino acid sequence (SEQ ID NO: 39):

$^1$A$_1$-X-Asn-Thr-$^5$Ala-Thr-Y-Ala-Thr-$^{10}$Gln-Arg-Leu-B$_1$-Asn-$^{15}$Phe-Leu-C$_1$-D$_1$-E$_1$-$^{20}$F$_1$-G$_1$-Asn-H$_1$-Gly-$^{25}$Pro-I$_1$-Leu-Pro-J$_1$-$^{30}$Thr-K$_1$-Val-Gly-Ser-$^{35}$Asn-Thr-Tyr-Z wherein
  $A_1$ is Lys, Ala, Ser or hydrogen;
  $B_1$ is Ala, Ser or Thr;
  $C_1$ is Val, Leu or Ile;
  $D_1$ is His or Arg;
  $E_1$ is Ser or Thr;
  $F_1$ is Ser, Thr, Gln or Asn;
  $G_1$ is Asn, Gln or His;
  $H_1$ is Phe, Leu or Tyr;
  $I_1$ is Ile, Val, Ala or Leu;
  $J_1$ is Ser, Pro or Thr;
  $K_1$ is Asn, Asp or Gln;
X and Y are independently selected residues having side chains which are chemically bonded to each other to form an intramolecular linkage, wherein said intramolecular linkage comprises a disulfide bond, a lactam or a thioether linkage; and Z is amino, alkylamino, dialkylamino, cycloalkylamino, arylamino, aralkylamino, alkyloxy, aryloxy or aralkyloxy; and provided that when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Val, $J_1$ is Pro, and $K_1$ is Asn; then one or more of $A_1$ to $K_1$ is a D-amino acid and Z is selected from the group consisting of alkylamino, dialkylamino, cycloalkylamino, arylamino, aralkylamino, alkyloxy, aryloxy or aralkyloxy.

ii) An agonist analogue of amylin having the amino acid sequence (SEQ ID No: 37):
$^1A_1$-X-Asn-Thr-$^5$Ala-Thr-Y-Ala-Thr-$^{10}$Gln-Arg-Leu-$B_1$-Asn-$^{15}$Phe-Leu-$C_1$-$D_1$-$E_1$-$^{20}F_1$-$G_1$-Asn-$H_1$-Gly-$^{25}$Pro-$I_1$-Leu-$J_1$-Pro-$^{30}$Thr-$K_1$-Val-Gly-Ser-$^{35}$Asn-Thr-Tyr-Z wherein
  $A_1$ is Lys, Ala, Ser or hydrogen;
  $B_1$ is Ala, Ser or Thr;
  $C_1$ is Val, Leu or Ile;
  $D_1$ is His or Arg;
  $E_1$ is Ser or Thr;
  $F_1$ is Ser, Thr, Gln or Asn;
  $G_1$ is Asn, Gln or His;
  $H_1$ is Phe, Leu or Tyr;
  $I_1$ is Ile, Val, Ala or Leu;
  $J_1$ is Ser, Pro, Leu, Ile or Thr;
  $K_1$ is Asn, Asp or Gln;
X and Y are independently selected residues having side chains which are chemically bonded to each other to form an intramolecular linkage, wherein said intramolecular linkage comprises a disulfide bond, a lactam or a thioether linkage; and Z is amino, alkylamino, dialkylamino, cycloalkylamino, arylamino, aralkylamino, alkyloxy, aryloxy or aralkyloxy; and provided than when
  (a) $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Val, $J_1$ is Pro and $K_1$ is Asn; or
  (b) $A_1$ is Lys, $B_1$ is Ala, $C_1$ is Val, $D_1$ is His, $E_1$ is Ser, $F_1$ is Asn, $G_1$ is Asn, $H_1$ is Leu, $I_1$ is Val, $J_1$ is Ser and $K_1$ is Asn;
then one or more of $A_1$ to $K_1$ is a D-amino acid and Z is selected from the group consisting of alkylamino, dialkylamino, cycloalkylamino, arylamino, aralkylamino, alkyloxy, aryloxy or aralkyloxy.

iii) An agonist analogue of amylin having the amino acid sequence(SEQ ID NO: 38):
$^1A_1$-X-Asn-Thr-$^5$Ala-Thr-Y-Ala-Thr-$^{10}$Gln-Arg-Leu-$B_1$-Asn-$^{15}$Phe-Leu-$C_1$-$D_1$-$E_1$-$^{20}F_1$-$G_1$-Asn-$H_1$-Gly-$^{25}I_1$-$J_1$-Leu-Pro-Pro-$^{30}$Thr-$K_1$-Val-Gly-Ser-$^{35}$Asn-Thr-Tyr-Z wherein
  $A_1$ is Lys, Ala, Ser or hydrogen;
  $B_1$ is Ala, Ser or Thr;
  $C_1$ is Val, Leu or Ile;
  $D_1$ is His or Arg;
  $E_1$ is Ser or Thr;
  $F_1$ is Ser, Thr, Gln or Asn;
  $G_1$ is Asn, Gln or His;
  $H_1$ is Phe, Leu or Tyr;
  $I_1$ is Ala or Pro;
  $J_1$ is Ile, Val, Ala or Leu;
  $K_1$ is Asn, Asp or Gln; X and Y are independently selected residues having side chains which are chemically bonded to each other to form an intramolecular linkage, wherein said intramolecular linkage comprises a disulfide bond, a lactam or a thioether linkage; and Z is amino, alkylamino, dialkylamino, cycloalkylamino, arylamino, aralkylamino, alkyloxy, aryloxy or aralkyloxy; and provided that when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Pro, $J_1$ is Val and $K_1$ is Asn; then one or more of $A_1$ to $K_1$ is a D-amino acid and Z is selected from the group consisting of alkylamino, dialkylamino, cycloalkylamino, arylamino, aralkylamino, alkyloxy, aryloxy or aralkyloxy.

iv) An agonist analogue of amylin having the amino acid sequence(SEQ ID NO: 39):
$^1A_1$-X-Asn-Thr-$^5$Ala-Thr-Y-Ala-Thr-$^{10}$Gln-Arg-Leu-$B_1$-Asn-$^{15}$Phe-Leu-$C_1$-$D_1$-$E_1$-$^{20}F_1$-$G_1$-Asn-$H_1$-Gly-$^{25}$Pro-$I_1$-Leu-Pro-Pro-$^{30}$Thr-$J_1$-Val-Gly-Ser-$^{35}$Asn-Thr-Tyr-Z wherein
  $A_1$ is Lys, Ala, Ser or hydrogen;
  $B_1$ is Ala, Ser or Thr;
  $C_1$ is Val, Leu or Ile;
  $D_1$ is His or Arg;
  $E_1$ is Ser or Thr;
  $F_1$ is Ser, Thr, Gln or Asn;
  $G_1$ is Asn, Gln or His;
  $H_1$ is Phe, Leu or Tyr;
  $I_1$ is Ile, Val, Ala or Leu;
  $J_1$ is Asn, Asp or Gln; X and Y are independently selected residues having side chains which are chemically bonded to each other to form an intramolecular linkage wherein said intramolecular linkage comprises a disulfide bond, a lactam or a thioether linkage; and Z is amino, alkylamino, dialkylamino, cycloalkylamino, arylamino, aralkylamino, alkyloxy, aryloxy or aralkyloxy; and provided that when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Val and $J_1$ is Asn; then one or more of $A_1$ to $K_1$ is a D-amino acid and Z is selected from the group consisting of alkylamino, dialkylamino, cycloalkylamino, arylamino, aralkylamino, alkyloxy, aryloxy or aralkyloxy.

Preferred amylin agonist compounds, des-$^1$Lys-h-amylin [SEQ. ID. NO:2], $^{28}$Pro-h-amylin [SEQ. ID. NO:3], $^{25,28,29}$Pro-h-amylin, $^{18}$Arg$^{25,28}$Pro-h-amylin [SEQ. ID. NO:4], and des-$^1$Lys$^{18}$Arg$^{25,28}$Pro-h-amylin [SEQ. ID. NO:5], all show amylin activity in vivo in treated test animals. In addition to having activities characteristic of amylin, certain preferred compounds have also been found to possess more desirable solubility and stability characteristics when compared to human amylin. These preferred compounds include $^{25}$Pro$^{26}$Val$^{28,29}$Pro-h-amylin [SEQ. ID. NO:6], $^{25,28,29}$Pro-h-amylin (also referred to herein as "AC-0137"), and $^{18}$Arg$^{25,28}$Pro-h-amylin.

The methods of the present invention employ an amylin or an amylin agonist, for example, amylin receptor agonists such as $^{18}$Arg$^{25,28}$Pro-h-amylin, des-$^1$Lys$^{18}$Arg$^{25,28}$Pro-h- amylin, $^{18}$Arg$^{25-28,29}$Pro-h-amylin [SEQ. ID. NO:7], des-$^{1}$Lys$^{18}$Arg$^{25,28,29}$Pro-h-amylin [SEQ. ID. NO:8], $^{25,28-29}$Pro-h-amylin, des-$^{1}$Lys$^{25,28,29}$Pro-h-amylin [SEQ. ID. NO:9], and $^{25}$Pro$^{26}$Val$^{28,29}$Pro-h-amylin. Examples of other suitable amylin agonists include:

$^{23}$Leu$^{25}$Pro$^{26}$Val$^{28,29}$Pro-h-amylin [SEQ. ID. NO.10];

$^{23}$Leu$^{25}$Pro$^{26}$Val$^{28}$Pro-h-amylin [SEQ. ID. NO.11];

des-$^{1}$Lys$^{23}$Leu$^{25}$Pro$^{26}$Val$^{28}$pro-h-amylin [SEQ. ID. NO.12];

$^{18}$Arg$^{23}$Leu$^{25}$Pro$^{26}$Val$^{28}$Pro-h-amylin [SEQ. ID. NO.13];

$^{18}$Arg$^{23}$Leu$^{25,28,29}$Pro-h-amylin [SEQ. ID. NO.14];

$^{18}$Arg$^{23}$Leu$^{25,28}$Pro-h-amylin [SEQ. ID. NO.15];

$^{17}$Ile$^{23}$Leu$^{25,28,29}$Pro-h-amylin [SEQ. ID. NO.16];

$^{17}$Ile$^{25,28,29}$Pro-h-amylin [SEQ. ID. NO.17];

des-$^{1}$Lys$^{17}$Ile$^{23}$Leu$^{25,28,29}$Pro-h-amylin [SEQ. ID. NO.18];

$^{17}$Ile$^{18}$Arg$^{23}$Leu-h-amylin; [SEQ. ID. NO.19];

$^{17}$Ile$^{18}$Arg$^{23}$Leu$^{26}$Val$^{29}$Pro-h-amylin [SEQ. ID. NO.20];

$^{17}$Ile$^{18}$Arg$^{23}$ Leu$^{25}$Pro$^{26}$Val$^{28,29}$Pro-h-amylin [SEQ. ID. NO.21];

$^{13}$Thr$^{21}$His$^{23}$Leu$^{26}$Ala$^{28}$Leu$^{29}$Pro$^{31}$Asp-h-amylin [SEQ. ID. NO.22];

$^{13}$Thr$^{21}$His$^{23}$Leu$^{26}$Ala$^{29}$Pro$^{31}$Asp-h-amylin [SEQ. ID. NO.23];

des-$^{1}$Lys$^{13}$Thr$^{21}$His$^{23}$Leu$^{26}$Ala$^{28}$Pro$^{31}$Asp-h-amylin [SEQ. ID. NO.24];

$^{13}$Thr$^{18}$Arg$^{21}$His$^{23}$Leu$^{26}$Ala$^{29}$Pro$^{31}$Asp-h-amylin [SEQ. ID. NO. 25];

$^{13}$Thr$^{18}$Arg$^{21}$His$^{23}$Leu$^{28,29}$Pro$^{31}$Asp-h-amylin [SEQ. ID. NO.26]; and, $^{13}$Thr$^{18}$Arg$^{21}$His$^{23}$Leu$^{25}$Pro$^{26}$Ala$^{28,29}$Pro$^{31}$Asp-h-amylin [SEQ. ID. NO.27].

Still further amylin agonists, including amylin agonist analogues, are disclosed, and methods for making and using amylin agonists are further specified, in commonly owned U.S. patent application Ser. No. 08/477,849, entitled "Novel Amylin Agonist Peptides and Uses Therefor" filed May 30, 1995 and corresponding PCT application Publication No. WO 93/10146, published May 27, 1993, the disclosures of which are hereby incorporated by this reference.

The activity of amylin agonists may be evaluated using certain biological assays described herein. The receptor binding assay can identify both candidate amylin agonists and antagonists and can be used to evaluate binding, while the rat gastric-emptying assay can be used to distinguish between amylin agonists and antagonists. Preferably, agonist compounds exhibit activity in the receptor binding assay on the order of less than about 1 to 5 nM, preferably less than about 1 nM and more preferably less than about 50 pM. In the in vivo rat gastric emptying assay these compounds preferably show ED$_{50}$ values on the order of less than about 100 to 1000 μg/rat.

The receptor binding assay is described in U.S. Pat. No. 5,264,372, issued Nov. 23, 1993, the disclosure of which is incorporated herein by reference. The receptor binding assay is a competition assay which measures the ability of compounds to bind specifically to membrane-bound amylin receptors. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand are analyzed by computer, using analyses by nonlinear regression to a 4-parameter logistic equation (Inplot program; GraphPAD Software, San Diego, Calif.) or the ALLFIT program of DeLean et. al. (ALLFIT, Version 2.7 (NIH, Bethesda, Md. 20892)). Munson, P. and Rodbard, D., *Anal. Biochem.* 107:220–239 (1980).

Amylins or amylin agonists can be identified, evaluated, or screened by their effects on gastric emptying using the methods described in U.S. application Ser. No. 08/118,381, filed Sep. 7, 1993, and U.S. application Ser. No. 08/302,069, filed Sep. 7, 1994 (corresponding to PCT Application, Publication No. WO 95/07098), the disclosures of which are hereby incorporated by reference, or other art-known or equivalent methods for determining gastric motility. One such method for use in identifying or evaluating the ability of a compound to slow gastric motility, comprises: (a) bringing together a test sample and a test system, said test sample comprising one or more test compounds, and said test system comprising a system for evaluating gastric motility, said system being characterized in that it exhibits, for example, elevated plasma label in response to the intragastric introduction to said system of that label; and, (b) determining the presence or amount of a rise in plasma label in said system. Positive and/or negative controls may be used as well. Optionally, a predetermined amount of amylin antagonist (e.g., $^{8-32}$salmon calcitonin [SEQ ID. NO. 28]) may be added to the test system.

Amylin agonists such as those described above are prepared using standard solid-phase peptide synthesis techniques and preferably an automated or semiautomated peptide synthesizer. Typically, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer are purchased from Applied Biosystems Inc. (Foster City, Calif.), unless otherwise indicated. The side-chain protected amino acids are purchased from Applied Biosystems, Inc. and include the following: Boc-Arg(Mts), Fmoc-Arg(Pmc), Boc-Thr(Bzl), Fmoc-Thr(t-Bu), Boc-Ser (Bzl), Fmoc-Ser(t-Bu), Boc-Tyr(BrZ), Fmoc-Tyr(t-Bu), Boc-Lys(Cl-Z), Fmoc-Lys(Boc), Boc-Glu(Bzl), Fmoc-Glu (t-Bu), Fmoc-His(Trt), Fmoc-Asn(Trt), and Fmoc-Gln(Trt). Boc-His(BOM) is purchased from Applied Biosystems, Inc. or Bachem Inc. (Torrance, Calif.). Anisole, methylsulfide, phenol, ethanedithiol, and thioanisole are obtained from Aldrich Chemical Company (Milwaukee, Wis.). Air Products and Chemicals (Allentown, Pa.) supplies HF. Ethyl ether, acetic acid and methanol are purchased from Fisher Scientific (Pittsburgh, Pa.).

Solid phase peptide synthesis is carried out with an automatic peptide synthesizer (Model 430A, Applied Biosystems Inc., Foster City, Calif.) using the NMP/HOBt (Option 1) system and Tboc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins are cleaved with HF (−5° C. to 0° C., 1 hour). The peptide is extracted from the resin with alternating water and acetic acid, and the filtrates are lyophilized. The Fmoc-peptide resins are cleaved according to standard methods (*Introduction to Cleavage Techniques*, Applied Biosystems, Inc., 1990, pp. 6–12). Some peptides are also assembled using an Advanced Chem Tech Synthesizer (Model MPS 350, Louisville, Ky.). Peptides are purified by RP-HPLC (preparative and analytical) using a Waters Delta Prep 3000 system. A C4, C8 or C18 preparative column (10 μ, 2.2×25 cm; Vydac, Hesperia, Calif.) is used to isolate peptides, and purity is determined using a C4, C8 or C18 analytical column (5 μ, 0.46×25 cm; Vydac). Solvents (A=0.1% TFA/water and B=0.1% TFA/$CH_3CN$) are delivered to the analytical column at a flowrate of 1.0 ml/min and to the preparative column at 15 ml/min. Amino acid analyses are performed on the Waters Pico Tag system and processed using the Maxima program. The peptides are hydrolyzed by vapor-phase acid hydrolysis (115° C., 20–24 h). Hydrolysates are derivatized and analyzed by standard methods (Cohen, S. A., Meys, M., and Tarrin, T. L. (1989), *The Pico Tag Method: A Manual of Advanced Techniques for Amino Acid Analysis*, pp. 11–52, Millipore Corporation, Milford, Mass.). Fast atom bombardment analysis is carried out by M-Scan, Incorporated (West Chester, Pa.). Mass calibration is performed using cesium iodide or cesium iodide/glycerol. Plasma desorption ionization analysis using time of flight detection is carried out on an Applied Biosystems Bio-Ion 20 mass spectrometer.

Peptide compounds useful in the claimed methods may also be prepared using recombinant DNA techniques, using methods now known in the art. See, e.g., Sambrook et al., *Molecular Cloning: A Laboratory Manual*, 2d Ed., Cold Spring Harbor (1989).

The compounds referenced above form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Compositions useful in the invention may conveniently be provided in the form of formulations suitable for parenteral (including, intramuscular and subcutaneous) or nasal or transdermal, and/or suitably encapsulated or otherwise prepared by another known methods for oral administration. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988).

Compounds useful in the invention can be provided as parenteral compositions for injection or infusion. Preferably, they are dissolved in an aqueous carrier, for example, in an isotonic buffer solution at a pH of about 4.3 to 7.4. These compositions may be sterilized by conventional sterilization techniques, or may be sterile filtered. The compositions may contain pharmaceutically acceptable auxiliary substances as required to stabilize the formulation, such as pH buffering agents. Useful buffers include for example, sodium acetate/ acetic acid buffers. A form of repository or "depot" slow release preparation may be used so that therapeutically effective amounts of the preparation are delivered into the bloodstream over many hours or days following transdermal injection or delivery.

Preferably, these parenteral dosage forms are prepared according to the U.S. Provisional Patent Application Ser. No. 60/231,182 filed Jan. 7, 1997, entitled "Parenteral, Liquid Formulations for Amylin Agonist Peptides," and include approximately 0.01 to 0.2 w/v %, respectively, of an amylin and/or an amylin agonist in an aqueous system along with approximately 0.02 to 0.5 w/v % of an acetate, phosphate, citrate or glutamate buffer to obtain a pH of the final composition of approximately 3.0 to 6.0 (more preferably 3.0 to 5.5), as well as approximately 1.0 to 10 w/v % of a carbohydrate or polyhydric alcohol stabilizer in an aqueous continuous phase. Approximately 0.005 to 1.0 w/v % of an antimicrobial preservative selected from the group consisting of m-cresol, benzyl alcohol, methyl, ethyl, propyl and butyl parabens and phenol is also present in the preferred formulation of product designed to allow the patient to withdraw multiple doses. A sufficient amount of water for injection is used to obtain the desired concentration of solution. Sodium chloride, as well as other excipients, may also be present, if desired. Such excipients, however, must maintain the overall stability of the amylin, or an amylin agonist. Most preferably, in the amylin and/or amylin agonist formulation for parenteral administration, the polyhydric alcohol is mannitol, the buffer is an acetate buffer, the preservative is approximately 0.1 to 0.3 w/v of m-cresol, and the pH is approximately 3.7 to 4.3.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an amylin or amylin agonist, for example, an amylin agonist with or without an NSAID which will be effective in one or multiple doses to control pain, inflammation, body temperature, blood coagulability, or other targeted biological response at the selected level. Therapeutically effective amounts of an amylin or amylin agonist are those that will alleviate the targeted symptom, or achieve the desired level of control. As will be recognized by those in the field, an effective amount of therapeutic agent will vary with many factors including the age and weight of the patient, the patient's physical condition, the action to be obtained and other factors.

The therapeutically effective daily dose of amylin or amylin agonist, for the treatment of gastritis and ulcers including h-amylin, $^{18}$Arg$^{25,28}$Pro-h-amylin, des-$^{1}$Lys$^{18}$Arg$^{25,28}$Pro-h-amylin, $^{18}$Arg$^{25,28,29}$Pro-h-amylin, des-$^{1}$Lys$^{18}$Arg-$^{25,28,29}$Pro-h-amylin, $^{25,28,29}$Pro-h-amylin, des-$^{1}$Lys$^{25,28,29}$Pro-h-amylin, and $^{25}$Pro$^{26}$Val$^{28,29}$Pro-h-amylin, will typically be in the range of 0.01 µg/kg/day to about 10 µg/kg/day, preferably between about 0.05 µg/kg/day to about 6.0 µg/kg/day, more preferably between about 1–6 µg/kg/day and even more preferably between about 0.5 µg/kg/day to about 4.0 µg/kg/day administered in single or divided doses.

The effective daily dose of amylin or amylin agonist in combination with an NSAID to relieve pain, thereby achieving a synergistic effect, including h-amylin, $^{18}$Arg$^{25,28}$Pro-h-amylin, des-$^{1}$Lys$^{18}$Arg$^{25,28}$Pro-h-amylin, $^{18}$Arg$^{25,28,29}$Pro-h-amylin, des-$^{1}$Lys$^{18}$Arg-$^{25,28,29}$Pro-h-amylin, $^{25,28,29}$Pro-h-amylin, des-$^{1}$Lys$^{25,28,29}$Pro-h-amylin, and $^{25}$Pro$^{26}$Val$^{28,29}$Pro-h-amylin, will typically be in the range of 0.01 µg/kg/day to about 10 µg/kg/day, preferably between about 0.05 µg/kg/day to about 6.0 µg/kg/day more preferably between about 1–6 µg/kg/day and even more preferably between about 0.5 µg/kg/day to about 4.0 µg/kg/day administered in single or divided doses. For these indications, the effective daily dose of the NSAID would depend on the agent used, and is comparable to the doses when NSAIDs are used alone. For example, daily doses for salicylate (aspirin) are 150 mg-3.5 g per day, for phenylbutazone 100 mg–600 mg per day, for indomethacin 50 mg–200 mg per day, and for acetaminophen 3 g–6 g per day.

The effective daily dose of amylin or amylin agonist to reduce the adverse gastric effects of the administration of an NSAID, including h-amylin, $^{18}$Arg$^{25,28}$Pro-h-amylin, des-$^{1}$Lys$^{18}$Arg$^{25,28}$Pro-h-amylin, $^{18}$Arg$^{25,28,29}$Pro-h-amylin, des-$^{1}$Lys$^{18}$Arg-$^{25,28,29}$Pro-h-amylin, $^{25,28,29}$Pro-h-amylin, des-$^{1}$Lys$^{25,28,29}$Pro-h-amylin, and $^{25}$Pro$^{26}$Val$^{28,29}$Pro-h-amylin, will typically be in the range of 0.01 µg/kg/day to about 10 µg/kg/day, preferably between about 0.05 µg/kg/day to about 6.0 µg/kg/day more preferably between about 1–6 µg/kg/day and even more preferably between about 0.5 µg/kg/day to about 4.0 µg/kg/day administered in single or divided doses. For these indications, the effective daily dose of the NSAID would depend on the agent used, and is comparable to the doses when NSAIDs are used alone. For example, daily doses for salicylate (aspirin) are 150 mg–3.5 g per day, for phenylbutazone 100 mg–600 mg per day, for indomethacin 50 mg–200 mg per day, and for acetaminophen 3 g–6 g per day.

The exact dose to be administered for each indication is determined by the attending clinician and is dependent upon where the particular compound lies within the above quoted range, as well as upon the age, weight and condition of the individual. Those of skill in the art will recognize that other non-daily doses may also be administered. Administration should begin at the first sign of symptoms in the case of gastritis, ulcers or pain, or at the time it is determined that the subject should begin NSAID therapy. Administration may be by injection, preferably subcutaneous or intramuscular. Administration may also be nasally or transdermally. Orally active compounds may be taken orally, however dosages should be adjusted based on their potencies and bioavailabilities, as appropriate.

The following Examples are illustrative, but not limiting of the methods of the present invention. Other suitable amylins and amylin agonists that may be adapted for use in the claimed methods are also appropriate and are within the spirit and scope of the invention.

EXAMPLE 1

Gastroprotective Properties of Amylin

The gastroprotective properties of amylin in an animal model for gastritis—the ethanol gavaged rat—are described in this example.

The effect of amylin on the induction of experimental mucosal damage in rats by gavage of 1 ml absolute ethanol was examined. Mucosal damage was scored between 0 (no damage) and 5 (100% of stomach covered by hyperemia and ulceration) by investigators blinded to the treatment. Rat amylin in saline was injected subcutaneously into fasted conscious male Harlan Sprague Dawley rats at doses of 0, 0.001, 0.01, 0.1, 0.3, 1, 3 or 10 µg (n=12, 5, 5, 5, 9, 9, 5, 6 respectively) 5 min before gavage. Mucosal damage, calculated as percent of scores in the saline-treated controls were, with the above rising subcutaneous doses, respectively: 100.0±8.3%, 95.3±15.2%, 76.6±13.8%, 70.1±10.7%*, 33.9±7.7%, 59.6±5.8%, 35.6±11.5%, 32.9±8.3% (*$P<0.05$, ** $P<0.001$ vs saline control). That is, amylin reduced the injury score by up to 67%, as observed with the 10 µg dose. The $ED_{50}$ for the gastroprotective effect of amylin in this experimental system was 0.036 µg/rat ±0.4 log units. The 50% gastroprotective dose of rat amylin (0.036 µg/rat) was predicted to increase circulating amylin concentrations by 1.8±0.4 pM. This prediction was obtained by applying the published relationship between injected subcutaneous dose and peak plasma concentration in rats. Young, A. A. et al., *Drug Devel. Res.* 37:231–48 (1996). Changes in plasma concentration of amylin of 1.8 pM is within the range of fluctuations reported to occur in normal rodents, indicating that endogenous circulating amylin is likely to exert a tonic gastroprotective effect. Mimicking this physiological effect is unlikely to result in unwanted side effects, as is often the case with administration of unphysiological xenobiotics. The absence of side effects enhances the utility of amylin agonists used for the purposes and in the manner specified herein.

EXAMPLE 2

Time Course of Amylin or Amylin Agonist Analgesic Action

Male Swiss Webster mice (NIH/Sw) obtained from Harlan (Madison, Wis.) and weighing 20–35 g are group housed with free access to food and water and maintained in a stable environment (12:12 light:dark cycle; 23±1° C.). All animals are habituated to the test room for at least one day prior to any experimentation, and are tested once between 07:30 and 14:00.

All drugs are dissolved in physiological saline, and given in a dose volume 10 ml/kg body weight.

The mouse writhing assay procedure used is a modification of a procedure disclosed in Hendershot and Forsaith, *J. Pharmacol. Expt. Therap.*, 125:237–240 (1959). Each mouse is allowed to habituate to the observation box for at least 15 minutes prior to testing. Each mouse is given an intraperitoneal injection of a 2% acetic acid solution to produce a writhing reaction, characterized by a wave of contraction of the abdominal musculature followed by the extension of the hind limbs. The number of writhes per animal is counted during a 10-minute interval starting 5 minutes after acetic acid injection.

0.1 mg/kg of amylin or amylin agonist is administered subcutaneously (sc) or intraperitoneally (ip) at 5, 15, 30 and 60 minutes prior to acetic acid injection in mice. Saline injections may be used as a negative control. An NSAID, such as salicylate may be used as a positive control.

To determine the time course of an amylin or amylin agonist action on visceral pain, the number of writhes per 10 minute period beginning 5 minutes after acetic acid injection are determined for each administration of amylin or amylin agonist and compared to saline-treated animals. To determine the enhancement of NSAID activity in relieving pain, time courses of amylin or amylin agonist administered in conjunction with an NSAID, and an NSAID administered alone, are compared.

EXAMPLE 3

Dose Response of Amylin Action

The same experimental procedures used in the experiments described in Example 2 are used to determine the dose response of an amylin or amylin agonist in relieving pain, either alone or in conjunction with an NSAID. Subcutaneous and intraperitoneal injections of amylin or amylin agonist (0.001, 0.003, 0.01, 0.1, 1.0 and 10.0 mg/kg) are given 30 minutes prior to acetic acid injection. Saline may be used as a negative control. An NSAID such as salicylate may be used as a positive control.

EXAMPLE 4

Isobologram Analysis of Interaction of Analgesic Effects of Amylin and NSAIDS

To further characterize the interaction between amylin and an NSAID, the results of the writhing studies may be graphed in isobolograms according to the method of Berenbaum, "The expected effect of a combination of agents: the general solution," *J. Theor. Biol.* 114:413 (1985). The isobologram is a quantitative method for measuring interactions between dosages of drugs that are equieffective in relationship to a common pharmacological endpoint to indicate synergy, additive effect or antagonism. In this instance, the writhing test may be used to estimate a common level of analgesic dose-ratio combination. In an isobologram, areas of dose additional, synergism and antagonism are clearly defined by reference to a theoretical straight (addition) line connecting the points on each axis. According to the isobologram theory, any points falling under the addition line represent enhanced analgesic activity and any points located above the line represent diminished analgesic activity.

EXAMPLE 5

Preparation of $^{25,28,29}$Pro-h-Amylin [SEQ. ID. NO.1]

Solid phase synthesis of $^{25,28,29}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,949$.

EXAMPLE 6

Preparation of $^{18}$Arg$^{25,28,29}$Pro-h-Amylin [SEQ. ID. NO.7]

Solid phase synthesis of $^{18}$Arg$^{25,28,29}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{18}$Arg$^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,971$.

EXAMPLE 7

Preparation of $^{18}$Arg$^{25,28}$Pro-h-Amylin [SEQ. ID. NO.4]

Solid phase synthesis of $^{18}$Arg$^{25,28}$Pro-h-amylin using methylbenzhydrylamine anchor-bond resin and $N^\alpha$-Boc/benzyl-side chain protection was carried out by standard peptide synthesis methods. The $^{2,7}$-[disulfide] amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{18}$Arg$^{25,28}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,959$.

EXAMPLE 8

Receptor Binding Assay

Evaluation of the binding of compounds to amylin receptors was carried out as follows. $^{125}$I-rat amylin (Bolton-Hunter labeled at the N-terminal lysine) was purchased from Amersham Corporation (Arlington Heights, Ill.). Specific activities at time of use ranged from 1950 to 2000 Ci/mmol. Unlabeled peptides were obtained from BACHEM Inc. (Torrance, Calif.) and Peninsula Laboratories (Belmont, Calif.).

Male Sprague-Dawley rats (200–250) grams were sacrificed by decapitation. Brains were removed to cold phosphate-buffered saline (PBS). From the ventral surface, cuts were made rostral to the hypothalamus, bounded laterally by the olfactory tracts and extending at a 45° angle medially from these tracts. This basal forebrain tissue, containing the nucleus accumbens and surrounding regions, was weighed and homogenized in ice-cold 20 mM HEPES buffer (20 mM HEPES acid, pH adjusted to 7.4 with NaOH at 23° C.). Membranes were washed three times in fresh buffer by centrifugation for 15 minutes at 48,000× g. The final membrane pellet was resuspended in 20 mM HEPES buffer containing 0.2 mM phenylmethylsulfonyl fluoride (PMSF).

To measure $^{125}$I-amylin binding, membranes from 4 mg original wet weight of tissue were incubated with 125I-amylin at 12–16 pM in 20 mM HEPES buffer containing 0.5 mg/ml bacitracin, 0.5 mg/ml bovine serum albumin, and 0.2 mM PMSF. Solutions were incubated for 60 minutes at 23° C. Incubations were terminated by filtration through GF/B glass fiber filters (Whatman Inc., Clifton, N.J.) which had been presoaked for 4 hours in 0.3% poylethyleneimine in order to reduce nonspecific binding of radiolabeled peptides. Filters were washed immediately before filtration with 5 ml cold PBS, and immediately after filtration with 15 ml cold PBS. Filters were removed and radioactivity assessed in a gamma-counter at a counting efficiency of 77 %. Competition curves were generated by measuring binding in the presence of $10^{-12}$ to $10^{-6}$ M unlabeled test compound and were analyzed by nonlinear regression using a 4-parameter logistic equation (Inplot program; GraphPAD Software, San Diego).

In this assay, purified human amylin binds to its receptor at a measured $IC_{50}$ of about 50 pM. Results for test compounds are set forth in Table I, showing that each of the compounds has significant receptor binding activity.

TABLE I

| $EC_{50}$ (nM) | | Receptor Binding Assay $IC_{50}$ (pM) |
|---|---|---|
| 1) $^{28}$Pro-h-Amylin | [SEQ. ID. NO. 3] | 15.0 |
| 2) $^{25}$Pro$^{26}$Val$^{28,29}$Pro-h-Amylin | [SEQ. ID. NO. 6] | 18.0 |
| 3) $^{2,7}$Cyclo-[$^2$Asp,$^7$Lys]-h-Amylin | [SEQ. ID. NO. 29] | 310.0 |
| 4) $^{2-37}$h-Amylin | [SEQ. ID. NO. 30] | 236.0 |
| 5) $^1$Ala-h-Amylin | [SEQ. ID. NO. 31] | 148.0 |
| 6) $^1$Ser-h-Amylin | [SEQ. ID. NO. 32] | 33.0 |
| 7) $^{29}$Pro-h-Amylin | [SEQ. ID. NO. 33] | 64.0 |
| 8) $^{25,28}$Pro-h-Amylin | [SEQ. ID. NO. 34] | 26.0 |
| 9) des-$^1$Lys$^{25,28}$Pro-h-Amylin | [SEQ. ID. NO. 35] | 85.0 |
| 10) $^{18}$Arg$^{25,28}$Pro-h-Amylin | [SEQ. ID. NO. 4] | 32.0 |
| 11) des-$^1$Lys$^{18}$Arg$^{25,28}$Pro-h-Amylin | [SEQ. ID. NO. 5] | 82.0 |
| 12) $^{18}$Arg$^{25,28,29}$Pro-h-Amylin | [SEQ. ID. NO. 7] | 21.0 |
| 13) des-$^1$Lys$^{18}$Arg$^{25,28,29}$Pro-h-Amylin | [SEQ. ID. NO. 8] | 21.0 |
| 14) $^{25,28,29}$Pro-h-Amylin | [SEQ. ID. NO. 1] | 10.0 |
| 15) des-$^1$Lys$^{25,28,29}$Pro-h-Amylin | [SEQ. ID. NO. 9] | 14.0 |

EXAMPLE 9

Phenol Red Gastric Emptying Assay

Gastric emptying was measured using a modification (Plourde et al., Life Sci. 53:857–862 (1993)) of the original method of Scarpignato et al. (Arch. Int. Pharmacodyn. Ther. 246:286–295 (1980)). Briefly, conscious rats received by gavage. 1.5 mL of an acoloric gel containing 1.5% methyl cellulose (M-0262, Sigma Chemical Co., St. Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In most experiments, the stomach was clear. In other experiments, particulate gastric contents were centrifuged to clear the solution for absorbance measurements. Where the diluted gastric contents remained turbid, the spectroscopic absorbance due to phenol red was derived as the difference between that present in alkaline vs acetified diluent. In separate experiments on 7 rats, the stomach and small intestine were both excised and opened into an alkaline solution. The quantity of phenol red that could be recovered from the upper gastrointestinal tact within 29 minutes of gavage was 89±4%; dye which appeared to bind irrecoverably to the gut luminal surface may have accounted for the balance. To compensate for this small loss, percent of stomach contents remaining after 20 minutes were expressed as a fraction of the gastric contents recovered from control rats sacrificed immediately after gavage in the same experiment. Percent gastric emptying contents remaining=(absorbance at 20 min)/(absorbance at 0 min). Dose response curves for gastric emptying were fitted to a 4-parameter logistic model using a least-squares iterative routine (ALLFIT, v2.7, NIH, Bethesda, Md.) to derive $ED_{50}$s. Since $ED_{50}$ is log-normally distributed, it is expressed ± standard error of the logarithm. Pairwise comparisons were performed using one-way analysis of variance and the Student-Newman-Keuls multiple comparisons test (Instat v2.0, GraphPad Software, San Diego, Calif.) using P<0.05 as the level of significance.

In dose response studies, rat amylin (Bachem, Torrance, Calif.) dissolved in 0.15M saline, was administered as a 0.1 mL subcutaneous bolus in doses of 0, 0.01, 0.1, 1, 10 or 100 μg 5 minutes before gavage in Harlan Sprague Dawley (non-diabetic) rats fasted 20 hours and diabetic BB rats fasted 6 hours. When subcutaneous amylin injections were given 5 minutes before gavage with phenol red indicator, there was a dose-dependent suppression of gastric emptying (data not shown). Suppression of gastric emptying was complete in normal HSD rats administered 1 μg of amylin, and in diabetic rats administered 10 μg (P=0.22, 0.14). The $ED_{50}$ for inhibition of gastric emptying in normal rats was 0.43 μg (0.60 nmol/kg)±0.19 log units, and was 2.2 μ (2.3 nmol/kg)±0.18 log units in diabetic rats.

EXAMPLE 10

Tritiated Glucose Gastric Emptying Assay

Conscious, non-fasted, Harlan Sprague Dawley rats were restrained by the tail, the tip of which was anesthetized using 2% lidocaine. Tritium in plasma separated from tail blood collected 0, 15, 30, 60, 90 and 120 minutes after gavage was detected in a beta counter. Rats were injected subcutaneously with 0.1 mL saline containing 0, 0.1, 0.3, 1, 10 or 100 μg of rat amylin 1 minute before gavage (n=8,7,5,5,5, respectively). After gavage of saline pre-injected rats with tritiated glucose, plasma tritium increased rapidly (t ½ of about 8 minutes) to an asymptote that slowly declined. Subcutaneous injection with amylin dose-dependently slowed and/or delayed the absorption of the label. Plasma tritium activity was integrated over 30 minutes to obtain the areas under the curve plotted as a function of amylin dose.

The $ED_{50}$ derived from the logistic fit was 0.35 µg of amylin.

What is claimed is:

1. A method for treating or preventing gastritis in a subject in need thereof, comprising peripherally administering to said subject a therapeutically effective amount of an amylin or an amylin agonist, wherein said amylin agonist is not a calcitonin or a CGRP.

2. A method for treating or preventing gastric ulceration in a subject in need thereof, comprising peripherally administering to said subject a therapeutically effective amount of amylin or an amylin agonist, wherein said amylin agonist is not a calcitonin or a CGRP.

3. A method of treating gastritis or gastric ulceration in a subject in need thereof by peripherally administering an amylin or an amylin agonist, wherein said amylin agonist is not a calcitonin or a CGRP, and wherein said amylin or amylin agonist has an $IC_{50}$ of about 5 nM or less in a rat receptor binding assay.

4. A method of treating or preventing gastritis or gastric ulceration, which is induced by ethanol or a non-steroidal anti-inflammatory compound, in a subject in need thereof by peripherally administering an amylin or an amylin agonist, wherein said amylin agonist is not a calcitonin or a CGRP, and wherein said amylin or amylin agonist has an $IC_{50}$ of about 5 nM or less in a rat receptor binding assay.

5. A method for treating or preventing gastritis in a subject, comprising:
   peripherally administering to said subject a therapeutically effective amount of an amylin or an amylin agonist, wherein said amylin agonist is not a calcitonin or a CGRP; and
   administering a non-steroidal anti-inflammatory drug.

6. A method for treating or preventing gastric ulceration in a subject, comprising:

peripherally administering to said subject a therapeutically effective amount of an amylin or an amylin agonist, wherein said amylin agonist is not a calcitonin or a CGRP; and administering a non-steroidal anti-inflammatory drug.

7. A method according to claim 1, 2, 3, or 4, wherein the amylin or the amylin agonist has an $IC_{50}$ value in a rat receptor binding assay of less than about 50 pM.

8. A method for treating gastritis in a subject, comprising peripherally administering to said subject a therapeutically effective amount of an amylin or an amylin agonist, wherein said amylin agonist is not a calcitonin or a CGRP.

9. A method for treating gastric ulceration in a subject, comprising peripherally administering to said subject a therapeutically effective amount of an amylin or an amylin agonist, wherein said amylin agonist is not a calcitonin or a CGRP.

10. The method of claim 1, 2, 4, 8, or 9, further comprising administering a non-steroidal anti-inflammatory drug.

11. The method according to any of claims 1–2, wherein said subject is human.

12. The method of according to any of claims 1–2, wherein said amylin or amylin agonist is administered by a route selected from the group consisting of nasal, oral, pulmonary, transdermal, and buccal administration.

13. The method according to any of claims 1–2 wherein said amylin agonist is selectyed from the group consisting of $^{18}$Arg$^{25,28}$Pro-h-amylin [SEQ. ID. NO. 4], des-$^{1}$Lys$^{18}$Arg$^{25,28}$Pro-h-amylin [SEQ. ID. NO. 5], $^{18}$Arg$^{25-28,29}$Pro-h-amylin [SEQ. ID. NO. 7], des-$^{1}$Lys$^{18}$Arg$^{25,28,29}$Pro-h-amylin [SEQ. ID. NO. 8], $^{25,28-29}$Pro-h-amylin [SEQ. ID. NO. 1], des-$^{1}$Lys$^{25,28,29}$Pro-h-amylin [SEQ. ID. NO. 9], $^{25}$Pro$^{26}$Val$^{28,29}$Pro-h-amylin [SEQ. ID. NO. 6], $^{23}$Leu$^{25}$Pro$^{26}$Val$^{28,29}$Pro-h-amylin [SEQ. ID. NO. 10], $^{23}$Leu$^{25}$Pro$^{26}$Val$^{28}$Pro-h-amylin [SEQ. ID. NO. 11], des-$^{1}$Lys$^{23}$Leu$^{25}$Pro$^{26}$Val$^{28}$Pro-h-amylin [SEQ. ID. NO. 12], $^{18}$Arg$^{23}$Leu$^{25}$Pro$^{26}$Val$^{28}$Pro-h-amylin [SEQ. ID. NO. 13], $^{18}$Arg$^{23}$Leu$^{25,28,29}$Pro-h-amylin [SEQ. ID. NO. 14], $^{18}$Arg$^{23}$Leu$^{25,28}$pro-h-amylin [SEQ. ID. NO. 15], $^{17}$Ile$^{23}$Leu$^{25,28,29}$Pro-h-amylin [SEQ. ID. NO. 16], $^{17}$Ile$^{25,28,29}$Pro-h-amylin [SEQ. ID. NO. 17], des-$^{1}$Lys$^{17}$Ile$^{23}$Leu$^{25,28,29}$Pro-h-amylin [SEQ. ID. NO. 18], $^{17}$Ile$^{18}$Arg$^{23}$Leu-h-amylin [SEQ. ID. NO. 19], $^{17}$Ile$^{18}$Arg$^{23}$Leu$^{26}$Val$^{29}$Pro-h-amylin [SEQ. ID. NO. 20], $^{17}$Ile$^{18}$Arg$^{23}$Leu$^{25}$Pro$^{26}$Val$^{28,29}$Pro-h-amylin [SEQ. ID. NO. 21], $^{13}$Thr$^{21}$His$^{23}$Leu$^{26}$Ala$^{28}$Leu$^{29}$Pro$^{31}$Asp-h-amylin [SEQ. ID. NO. 22], $^{13}$Thr$^{21}$His$^{23}$Leu$^{26}$Ala$^{29}$Pro$^{31}$Asp-h-amylin [SEQ. ID. NO. 23], des-$^{1}$Lys$^{13}$Thr$^{21}$His$^{23}$Leu$^{26}$Ala$^{28}$Pro$^{31}$Asp-h-amylin [SEQ. ID. NO. 24], $^{13}$Thr$^{18}$Arg$^{21}$His$^{23}$Leu$^{26}$Ala$^{29}$Pro$^{31}$Asp-h-amylin [SEQ. ID. NO. 25], $^{13}$Thr$^{18}$Arg$^{21}$His$^{23}$Leu$^{28,29}$Pro$^{31}$Asp-h-amylin [SEQ. ID. NO. 26], and $^{13}$Thr$^{18}$Arg$^{21}$His$^{23}$Leu$^{25}$Pro$^{26}$Ala$^{28,29}$Pro$^{31}$Asp-h-amylin [SEQ. ID. NO. 27].

14. The method of claim 1, 2, 3, 4, 5, 6, 8, or 9, wherein said amylin agonist is $^{25,28,29}$Pro-h-amylin [SEQ. ID. NO. 1].

15. The method according to any of claims 1 or 2, wherein said gastritis or gastric ulceration is associated with the administration of a non-steroidal anti-inflammatory drug.

16. The method according to claim 10 wherein said non-steroidal anti-inflammatory agent is selected from the group consisting of salicylate, phenylbutazone, indomethacin, acetominophen, phenacetin, naproxen and ibuprofen.

17. The method of claim 1 or 2, wherein said amylin or amylin agonist is amylin.

18. The method of claim 1 or 2, wherein said $IC_{50}$ of said amylin or amylin agonist is about 5 nM or less in a rat receptor binding assay.

19. The method of claim 1 or 2 wherein said gastritis or gastric ulceration is induced by a member selected from the group consisting of ethanol and NSAIDs.

20. The method of claim 19 wherein said member is ethanol.

21. The method of claim 1, 2, 3, or 4, wherein said amylin or amylin agonist has an $IC_{50}$ of about 1 nM or less in a rat receptor binding assay.

22. The method according to claim 12 wherein said route is nasal.

23. The method according to claim 12 wherein said route is oral.

24. The method according to claim 12 wherein said route is pulmonary.

25. The method according to claim 12 wherein said route is transdermal.

26. The method according to claim 12 wherein said route is buccal.

* * * * *

UNITED STATES PATENT AND TRADEMARK OFFICE
CERTIFICATE OF CORRECTION

PATENT NO.         : 7,101,853 B2
APPLICATION NO. : 08/851965
DATED              : September 5, 2006
INVENTOR(S)        : Young et al.

It is certified that error appears in the above-identified patent and that said Letters Patent is hereby corrected as shown below:

In Claim Number 2 (column 49) at lines 59-60, please insert --an-- between "of" and "amylin".

Signed and Sealed this

Seventh Day of November, 2006

JON W. DUDAS
*Director of the United States Patent and Trademark Office*

SEQUENCE LISTING

```
<160> NUMBER OF SEQ ID NOS: 39

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 1

Lys Cys Asn Thr Ala Thr Cys Ala Thr Gln Arg Leu Ala Asn Phe Leu
 1               5                  10                  15

Val His Ser Ser Asn Asn Phe Gly Pro Ile Leu Pro Pro Thr Asn Val
                20                  25                  30

Gly Ser Asn Thr Tyr
            35

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 1 and 6
<220> FEATURE:
<221> NAME/KEY: MOD_RES
<222> LOCATION: (36)
<223> OTHER INFORMATION: amidated Tyr (Tyrosinamide)

<400> SEQUENCE: 2

Cys Asn Thr Ala Thr Cys Ala Thr Gln Arg Leu Ala Asn Phe Leu Val
 1               5                  10                  15

His Ser Ser Asn Asn Phe Gly Ala Ile Leu Ser Ser Thr Asn Val Gly
                20                  25                  30

Ser Asn Thr Tyr
            35

<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)
```

<400> SEQUENCE: 3

```
Lys Cys Asn Thr Ala Thr Cys Ala Thr Gln Arg Leu Ala Asn Phe Leu
  1               5                  10                  15

Val His Ser Ser Asn Asn Phe Gly Ala Ile Leu Pro Ser Thr Asn Val
             20                  25                  30

Gly Ser Asn Thr Tyr
             35
```

<210> SEQ ID NO 4
<211> LENGTH: 37
<212> TYPE: PRT
<213> ORGANISM: Artificial Sequence
<220> FEATURE:
<223> OTHER INFORMATION: Description of Artificial Sequence: Synthetic protein construct
<220> FEATURE:
<223> OTHER INFORMATION: Disulfide bridge between the Cys residues at positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 4

```
Lys Cys Asn Thr Ala Thr Cys Ala Thr Gln Arg Leu Ala Asn Phe Leu
  1               5                  10                  15

Val Arg Ser Ser Asn Asn Phe Gly Pro Ile Leu Pro Ser Thr Asn Val
             20                  25                  30

Gly Ser Asn Thr Tyr
             35
```

<210> SEQ ID NO 5
<211> LENGTH: 36
<212> TYPE: PRT
<213> ORGANISM: Artificial Sequence
<220> FEATURE:
<223> OTHER INFORMATION: Description of Artificial Sequence: Synthetic protein construct
<220> FEATURE:
<223> OTHER INFORMATION: Disulfide bridge between the Cys residues at positions 1 and 6
<220> FEATURE:
<221> NAME/KEY: MOD_RES
<222> LOCATION: (36)
<223> OTHER INFORMATION: amidated Tyr (Tyrosinamide)

<400> SEQUENCE: 5

```
Cys Asn Thr Ala Thr Cys Ala Thr Gln Arg Leu Ala Asn Phe Leu Val
  1               5                  10                  15

Arg Ser Ser Asn Asn Phe Gly Pro Ile Leu Pro Ser Thr Asn Val Gly
             20                  25                  30

Ser Asn Thr Tyr
             35
```

<210> SEQ ID NO 6
<211> LENGTH: 37
<212> TYPE: PRT
<213> ORGANISM: Artificial Sequence
<220> FEATURE:
<223> OTHER INFORMATION: Description of Artificial Sequence: Synthetic protein construct
<220> FEATURE:
<223> OTHER INFORMATION: Disulfide bridge between the Cys residues at positions 2 and 7
<220> FEATURE:
<221> NAME/KEY: MOD_RES
<222> LOCATION: (37)

<223> OTHER INFORMATION: amidated Tyr (Tyrosinamide)

<400> SEQUENCE: 6

```
Lys Cys Asn Thr Ala Thr Cys Ala Thr Gln Arg Leu Ala Asn Phe Leu
 1               5                  10                  15

Val His Ser Ser Asn Asn Phe Gly Pro Val Leu Pro Pro Thr Asn Val
                20                  25                  30

Gly Ser Asn Thr Tyr
                35
```

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic protein construct
<220> FEATURE:
<223> OTHER INFORMATION: Disulfide bridge between the Cys residues at positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 7

```
Lys Cys Asn Thr Ala Thr Cys Ala Thr Gln Arg Leu Ala Asn Phe Leu
 1               5                  10                  15

Val Arg Ser Ser Asn Asn Phe Gly Pro Ile Leu Pro Pro Thr Asn Val
                20                  25                  30

Gly Ser Asn Thr Tyr
                35
```

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence: Synthetic protein construct
<220> FEATURE:
<223> OTHER INFORMATION: Disulfide bridge between the Cys residues at positions 1 and 6
<220> FEATURE:
<221> NAME/KEY: MOD_RES
<222> LOCATION: (36)
<223> OTHER INFORMATION: amidated Tyr (Tyrosinamide)

<400> SEQUENCE: 8

```
Cys Asn Thr Ala Thr Cys Ala Thr Gln Arg Leu Ala Asn Phe Leu Val
 1               5                  10                  15

Arg Ser Ser Asn Asn Phe Gly Pro Ile Leu Pro Pro Thr Asn Val Gly
                20                  25                  30

Ser Asn Thr Tyr
                35
```

<210> SEQ ID NO 9
<211> LENGTH: 36
<212> TYPE: PRT
<213> ORGANISM: Artificial Sequence
<220> FEATURE:
<223> OTHER INFORMATION: Description of Artificial Sequence: Synthetic protein construct
<220> FEATURE:
<223> OTHER INFORMATION: Disulfide bridge between the Cys residues at positions 1 and 6
<220> FEATURE:

```
<221> NAME/KEY: MOD_RES
<222> LOCATION: (36)
<223> OTHER INFORMATION: amidated Tyr (Tyrosinamide)

<400> SEQUENCE: 9

Cys Asn Thr Ala Thr Cys Ala Thr Gln Arg Leu Ala Asn Phe Leu Val
 1               5                  10                  15

His Ser Ser Asn Asn Phe Gly Pro Ile Leu Pro Pro Thr Asn Val Gly
            20                  25                  30

Ser Asn Thr Tyr
        35

<210> SEQ ID NO 10
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 10

Lys Cys Asn Thr Ala Thr Cys Ala Thr Gln Arg Leu Ala Asn Phe Leu
 1               5                  10                  15

Val His Ser Ser Asn Asn Leu Gly Pro Val Leu Pro Pro Thr Asn Val
            20                  25                  30

Gly Ser Asn Thr Tyr
        35

<210> SEQ ID NO 11
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 11

Lys Cys Asn Thr Ala Thr Cys Ala Thr Gln Arg Leu Ala Asn Phe Leu
 1               5                  10                  15

Val His Ser Ser Asn Asn Leu Gly Pro Val Leu Pro Ser Thr Asn Val
            20                  25                  30

Gly Ser Asn Thr Tyr
        35

<210> SEQ ID NO 12
<211> LENGTH: 36
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
```

```
            positions 1 and 6
<220> FEATURE:
<221> NAME/KEY: MOD_RES
<222> LOCATION: (36)
<223> OTHER INFORMATION: amidated Tyr (Tyrosinamide)

<400> SEQUENCE: 12

Cys Asn Thr Ala Thr Cys Ala Thr Gln Arg Leu Ala Asn Phe Leu Val
  1               5                  10                  15

His Ser Ser Asn Asn Leu Gly Pro Val Leu Pro Ser Thr Asn Val Gly
             20                  25                  30

Ser Asn Thr Tyr
         35

<210> SEQ ID NO 13
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 13

Lys Cys Asn Thr Ala Thr Cys Ala Thr Gln Arg Leu Ala Asn Phe Leu
  1               5                  10                  15

Val Arg Ser Ser Asn Asn Leu Gly Pro Val Leu Pro Ser Thr Asn Val
             20                  25                  30

Gly Ser Asn Thr Tyr
         35

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 14

Lys Cys Asn Thr Ala Thr Cys Ala Thr Gln Arg Leu Ala Asn Phe Leu
  1               5                  10                  15

Val Arg Ser Ser Asn Asn Leu Gly Pro Ile Leu Pro Pro Thr Asn Val
             20                  25                  30

Gly Ser Asn Thr Tyr
         35

<210> SEQ ID NO 15
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
```

```
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 15

Lys Cys Asn Thr Ala Thr Cys Ala Thr Gln Arg Leu Ala Asn Phe Leu
 1               5                  10                  15

Val Arg Ser Ser Asn Asn Leu Gly Pro Ile Leu Pro Ser Thr Asn Val
            20                  25                  30

Gly Ser Asn Thr Tyr
            35

<210> SEQ ID NO 16
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 16

Lys Cys Asn Thr Ala Thr Cys Ala Thr Gln Arg Leu Ala Asn Phe Leu
 1               5                  10                  15

Ile His Ser Ser Asn Asn Leu Gly Pro Ile Leu Pro Pro Thr Asn Val
            20                  25                  30

Gly Ser Asn Thr Tyr
            35

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 17

Lys Cys Asn Thr Ala Thr Cys Ala Thr Gln Arg Leu Ala Asn Phe Leu
 1               5                  10                  15

Ile His Ser Ser Asn Asn Phe Gly Pro Ile Leu Pro Pro Thr Asn Val
            20                  25                  30

Gly Ser Asn Thr Tyr
            35

<210> SEQ ID NO 18
<211> LENGTH: 36
<212> TYPE: PRT
<213> ORGANISM: Artificial Sequence
<220> FEATURE:
```

<223> OTHER INFORMATION: Description of Artificial Sequence: Synthetic
      protein construct
<220> FEATURE:
<223> OTHER INFORMATION: Disulfide bridge between the Cys residues at
      positions 1 and 6
<220> FEATURE:
<221> NAME/KEY: MOD_RES
<222> LOCATION: (36)
<223> OTHER INFORMATION: amidated Tyr (Tyrosinamide)

<400> SEQUENCE: 18

Cys Asn Thr Ala Thr Cys Ala Thr Gln Arg Leu Ala Asn Phe Leu Ile
 1               5                  10                  15

His Ser Ser Asn Asn Leu Gly Pro Ile Leu Pro Pro Thr Asn Val Gly
            20                  25                  30

Ser Asn Thr Tyr
        35

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 19

Lys Cys Asn Thr Ala Thr Cys Ala Thr Gln Arg Leu Ala Asn Phe Leu
 1               5                  10                  15

Ile Arg Ser Ser Asn Asn Leu Gly Ala Ile Leu Ser Ser Thr Asn Val
            20                  25                  30

Gly Ser Asn Thr Tyr
        35

<210> SEQ ID NO 20
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 20

Lys Cys Asn Thr Ala Thr Cys Ala Thr Gln Arg Leu Ala Asn Phe Leu
 1               5                  10                  15

Ile Arg Ser Ser Asn Asn Leu Gly Ala Val Leu Ser Pro Thr Asn Val
            20                  25                  30

Gly Ser Asn Thr Tyr
        35

<210> SEQ ID NO 21
<211> LENGTH: 37
<212> TYPE: PRT

-continued

```
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 21

Lys Cys Asn Thr Ala Thr Cys Ala Thr Gln Arg Leu Ala Asn Phe Leu
  1               5                  10                  15

Ile Arg Ser Ser Asn Asn Leu Gly Pro Val Leu Pro Pro Thr Asn Val
             20                  25                  30

Gly Ser Asn Thr Tyr
             35

<210> SEQ ID NO 22
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 22

Lys Cys Asn Thr Ala Thr Cys Ala Thr Gln Arg Leu Thr Asn Phe Leu
  1               5                  10                  15

Val His Ser Ser His Asn Leu Gly Ala Ala Leu Leu Pro Thr Asp Val
             20                  25                  30

Gly Ser Asn Thr Tyr
             35

<210> SEQ ID NO 23
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 23

Lys Cys Asn Thr Ala Thr Cys Ala Thr Gln Arg Leu Thr Asn Phe Leu
  1               5                  10                  15

Val His Ser Ser His Asn Leu Gly Ala Ala Leu Ser Pro Thr Asp Val
             20                  25                  30

Gly Ser Asn Thr Tyr
             35

<210> SEQ ID NO 24
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 1 and 6
<220> FEATURE:
<221> NAME/KEY: MOD_RES
<222> LOCATION: (36)
<223> OTHER INFORMATION: amidated Tyr (Tyrosinamide)

<400> SEQUENCE: 24

Cys Asn Thr Ala Thr Cys Ala Thr Gln Arg Leu Thr Asn Phe Leu Val
 1               5                  10                  15

His Ser Ser His Asn Leu Gly Ala Ala Leu Pro Ser Thr Asp Val Gly
            20                  25                  30

Ser Asn Thr Tyr
        35

<210> SEQ ID NO 25
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 25

Lys Cys Asn Thr Ala Thr Cys Ala Thr Gln Arg Leu Thr Asn Phe Leu
 1               5                  10                  15

Val Arg Ser Ser His Asn Leu Gly Ala Ala Leu Ser Pro Thr Asp Val
            20                  25                  30

Gly Ser Asn Thr Tyr
        35

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 26

Lys Cys Asn Thr Ala Thr Cys Ala Thr Gln Arg Leu Thr Asn Phe Leu
 1               5                  10                  15

Val Arg Ser Ser His Asn Leu Gly Ala Ile Leu Pro Pro Thr Asp Val
            20                  25                  30

Gly Ser Asn Thr Tyr
        35
```

-continued

```
<210> SEQ ID NO 27
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 27

Lys Cys Asn Thr Ala Thr Cys Ala Thr Gln Arg Leu Thr Asn Phe Leu
 1               5                  10                  15

Val Arg Ser Ser His Asn Leu Gly Pro Ala Leu Pro Pro Thr Asp Val
             20                  25                  30

Gly Ser Asn Thr Tyr
         35

<210> SEQ ID NO 28
<211> LENGTH: 25
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<221> NAME/KEY: MOD_RES
<222> LOCATION: (25)
<223> OTHER INFORMATION: amidated Pro (Prolinamide)

<400> SEQUENCE: 28

Val Leu Gly Lys Leu Ser Gln Glu Leu His Lys Leu Gln Thr Tyr Pro
 1               5                  10                  15

Arg Thr Asn Thr Gly Ser Gly Thr Pro
             20                  25

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: 2,7 cyclo bridge
<220> FEATURE:
<221> NAME/KEY: MOD_RES
<222> LOCATION: (37)
<223> OTHER INFORMATION: amidated Tyr (Tyrosinamide)

<400> SEQUENCE: 29

Lys Asp Asn Thr Ala Thr Lys Ala Thr Gln Arg Leu Ala Asn Phe Leu
 1               5                  10                  15

Val His Ser Ser Asn Asn Phe Gly Ala Ile Leu Ser Ser Thr Asn Val
             20                  25                  30

Gly Ser Asn Thr Tyr
         35

<210> SEQ ID NO 30
<211> LENGTH: 36
<212> TYPE: PRT
<213> ORGANISM: Artificial Sequence
```

```
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 1 and 6
<220> FEATURE:
<221> NAME/KEY: MOD_RES
<222> LOCATION: (36)
<223> OTHER INFORMATION: amidated Tyr (Tyrosinamide)

<400> SEQUENCE: 30

Cys Asn Thr Ala Thr Cys Ala Thr Gln Arg Leu Ala Asn Phe Leu Val
 1               5                  10                  15

His Ser Ser Asn Asn Phe Gly Ala Ile Leu Ser Ser Thr Asn Val Gly
            20                  25                  30

Ser Asn Thr Tyr
        35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 31

Ala Cys Asn Thr Ala Thr Cys Ala Thr Gln Arg Leu Ala Asn Phe Leu
 1               5                  10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 32
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 32

Ser Cys Asn Thr Ala Thr Cys Ala Thr Gln Arg Leu Ala Asn Phe Leu
 1               5                  10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 33
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 33

Lys Cys Asn Thr Ala Thr Cys Ala Thr Gln Arg Leu Ala Asn Phe Leu
 1               5                  10                  15

Val His Ser Ser Asn Asn Phe Gly Ala Ile Leu Ser Pro Thr Asn Val
            20                  25                  30

Gly Ser Asn Thr Tyr
            35

<210> SEQ ID NO 34
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 2 and 7
<220> FEATURE:
<221> NAME/KEY: MOD_RES
<222> LOCATION: (37)
<223> OTHER INFORMATION: amidated Tyr (Tyrosinamide)

<400> SEQUENCE: 34

Lys Cys Asn Thr Ala Thr Cys Ala Thr Gln Arg Leu Ala Asn Phe Leu
 1               5                  10                  15

Val His Ser Ser Asn Asn Phe Gly Pro Ile Leu Pro Ser Thr Asn Val
            20                  25                  30

Gly Ser Asn Thr Tyr
            35

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<223> OTHER INFORMATION: Disulfide bridge between the Cys residues at
      positions 1 and 6
<220> FEATURE:
<221> NAME/KEY: MOD_RES
<222> LOCATION: (36)
<223> OTHER INFORMATION: amidated Tyr (Tyrosinamide)

<400> SEQUENCE: 35

Cys Asn Thr Ala Thr Cys Ala Thr Gln Arg Leu Ala Asn Phe Leu Val
 1               5                  10                  15

His Ser Ser Asn Asn Phe Gly Pro Ile Leu Pro Ser Thr Asn Val Gly
            20                  25                  30

Ser Asn Thr Tyr
        35
```

```
<210> SEQ ID NO 36
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<221> NAME/KEY: MOD_RES
<222> LOCATION: (1)
<223> OTHER INFORMATION: Lys, Ala, Ser or not present
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (13)
<223> OTHER INFORMATION: Ala, Ser, or Thr
<220> FEATURE:
<221> NAME/KEY: MOD_RES
<222> LOCATION: (17)
<223> OTHER INFORMATION: Val, Leu, or Ile
<220> FEATURE:
<221> NAME/KEY: MOD_RES
<222> LOCATION: (18)
<223> OTHER INFORMATION: His or Arg
<220> FEATURE:
<221> NAME/KEY: MOD_RES
<222> LOCATION: (19)
<223> OTHER INFORMATION: Ser or Thr
<220> FEATURE:
<221> NAME/KEY: MOD_RES
<222> LOCATION: (20)
<223> OTHER INFORMATION: Ser, Thr, Gln, or Asn
<220> FEATURE:
<221> NAME/KEY: MOD_RES
<222> LOCATION: (21)
<223> OTHER INFORMATION: Asn, Gln, or His
<220> FEATURE:
<221> NAME/KEY: MOD_RES
<222> LOCATION: (23)
<223> OTHER INFORMATION: Phe, Leu, or Tyr
<220> FEATURE:
<221> NAME/KEY: MOD_RES
<222> LOCATION: (26)
<223> OTHER INFORMATION: Ile, Val, Ala, or Leu
<220> FEATURE:
<221> NAME/KEY: MOD_RES
<222> LOCATION: (29)
<223> OTHER INFORMATION: Ser, Pro, or Thr
<220> FEATURE:
<221> NAME/KEY: MOD_RES
<222> LOCATION: (31)
<223> OTHER INFORMATION: Asn, Asp, or Gln
<220> FEATURE:
<223> OTHER INFORMATION: See specification as filed for detailed
      description of substitutions and preferred embodiments

<400> SEQUENCE: 36

Xaa Xaa Asn Thr Ala Thr Xaa Ala Thr Gln Arg Leu Xaa Asn Phe Leu
 1               5                  10                  15

Xaa Xaa Xaa Xaa Xaa Asn Xaa Gly Pro Xaa Leu Pro Xaa Thr Xaa Val
             20                  25                  30

Gly Ser Asn Thr Tyr
             35

<210> SEQ ID NO 37
<211> LENGTH: 37
<212> TYPE: PRT
<213> ORGANISM: Artificial Sequence
```

```
<220> FEATURE:
<223> OTHER INFORMATION: Description of Artificial Sequence: Synthetic
      protein construct
<220> FEATURE:
<221> NAME/KEY: MOD_RES
<222> LOCATION: (1)
<223> OTHER INFORMATION: Lys, Ala, Ser or not present
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (13)
<223> OTHER INFORMATION: Ala, Ser, or Thr
<220> FEATURE:
<221> NAME/KEY: MOD_RES
<222> LOCATION: (17)
<223> OTHER INFORMATION: Val, Leu, or Ile
<220> FEATURE:
<221> NAME/KEY: MOD_RES
<222> LOCATION: (18)
<223> OTHER INFORMATION: His or Arg
<220> FEATURE:
<221> NAME/KEY: MOD_RES
<222> LOCATION: (19)
<223> OTHER INFORMATION: Ser or Thr
<220> FEATURE:
<221> NAME/KEY: MOD_RES
<222> LOCATION: (20)
<223> OTHER INFORMATION: Ser, Thr, Gln, or Asn
<220> FEATURE:
<221> NAME/KEY: MOD_RES
<222> LOCATION: (21)
<223> OTHER INFORMATION: Asn, Gln, or His
<220> FEATURE:
<221> NAME/KEY: MOD_RES
<222> LOCATION: (23)
<223> OTHER INFORMATION: Phe, Leu, or Tyr
<220> FEATURE:
<221> NAME/KEY: MOD_RES
<222> LOCATION: (26)
<223> OTHER INFORMATION: Ile, Val, Ala, or Leu
<220> FEATURE:
<221> NAME/KEY: MOD_RES
<222> LOCATION: (28)
<223> OTHER INFORMATION: Ser, Pro, Leu, Ile, or Thr
<220> FEATURE:
<221> NAME/KEY: MOD_RES
<222> LOCATION: (31)
<223> OTHER INFORMATION: Asn, Asp, or Gln
<220> FEATURE:
<223> OTHER INFORMATION: See specification as filed for detailed
      description of substitutions and preferred embodiments

<400> SEQUENCE: 37

Xaa Xaa Asn Thr Ala Thr Xaa Ala Thr Gln Arg Leu Xaa Asn Phe Leu
 1               5                  10                  15

Xaa Xaa Xaa Xaa Xaa Asn Xaa Gly Pro Xaa Leu Xaa Pro Thr Xaa Val
            20                  25                  30

Gly Ser Asn Thr Tyr
            35

<210> SEQ ID NO 38
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
```

```
<221> NAME/KEY: MOD_RES
<222> LOCATION: (1)
<223> OTHER INFORMATION: Lys, Ala, Ser or not present
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (13)
<223> OTHER INFORMATION: Ala, Ser, or Thr
<220> FEATURE:
<221> NAME/KEY: MOD_RES
<222> LOCATION: (17)
<223> OTHER INFORMATION: Val, Leu, or Ile
<220> FEATURE:
<221> NAME/KEY: MOD_RES
<222> LOCATION: (18)
<223> OTHER INFORMATION: His or Arg
<220> FEATURE:
<221> NAME/KEY: MOD_RES
<222> LOCATION: (19)
<223> OTHER INFORMATION: Ser or Thr
<220> FEATURE:
<221> NAME/KEY: MOD_RES
<222> LOCATION: (20)
<223> OTHER INFORMATION: Ser, Thr, Gln, or Asn
<220> FEATURE:
<221> NAME/KEY: MOD_RES
<222> LOCATION: (21)
<223> OTHER INFORMATION: Asn, Gln, or His
<220> FEATURE:
<221> NAME/KEY: MOD_RES
<222> LOCATION: (23)
<223> OTHER INFORMATION: Phe, Leu, or Tyr
<220> FEATURE:
<221> NAME/KEY: MOD_RES
<222> LOCATION: (25)
<223> OTHER INFORMATION: Ala or Pro
<220> FEATURE:
<221> NAME/KEY: MOD_RES
<222> LOCATION: (26)
<223> OTHER INFORMATION: Ile, Val, Ala, or Leu
<220> FEATURE:
<221> NAME/KEY: MOD_RES
<222> LOCATION: (31)
<223> OTHER INFORMATION: Asn, Asp, or Gln
<220> FEATURE:
<223> OTHER INFORMATION: See specification as filed for detailed
      description of substitutions and preferred embodiments

<400> SEQUENCE: 38

Xaa Xaa Asn Thr Ala Thr Xaa Ala Thr Gln Arg Leu Xaa Asn Phe Leu
  1               5                  10                  15

Xaa Xaa Xaa Xaa Xaa Asn Xaa Gly Xaa Xaa Leu Pro Pro Thr Xaa Val
             20                  25                  30

Gly Ser Asn Thr Tyr
             35

<210> SEQ ID NO 39
<211> LENGTH: 37
<212> TYPE: PRT
<213> ORGANISM: Artificial Sequence
<220> FEATURE:
<223> OTHER INFORMATION: Description of Artificial Sequence: Synthetic
      protein construct
<220> FEATURE:
<221> NAME/KEY: MOD_RES
<222> LOCATION: (1)
<223> OTHER INFORMATION: Lys, Ala, Ser or not present
<220> FEATURE:
```

```
-continued

<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (13)
<223> OTHER INFORMATION: Ala, Ser, or Thr
<220> FEATURE:
<221> NAME/KEY: MOD_RES
<222> LOCATION: (17)
<223> OTHER INFORMATION: Val, Leu, or Ile
<220> FEATURE:
<221> NAME/KEY: MOD_RES
<222> LOCATION: (18)
<223> OTHER INFORMATION: His or Arg
<220> FEATURE:
<221> NAME/KEY: MOD_RES
<222> LOCATION: (19)
<223> OTHER INFORMATION: Ser or Thr
<220> FEATURE:
<221> NAME/KEY: MOD_RES
<222> LOCATION: (20)
<223> OTHER INFORMATION: Ser, Thr, Gln, or Asn
<220> FEATURE:
<221> NAME/KEY: MOD_RES
<222> LOCATION: (21)
<223> OTHER INFORMATION: Asn, Gln, or His
<220> FEATURE:
<221> NAME/KEY: MOD_RES
<222> LOCATION: (23)
<223> OTHER INFORMATION: Phe, Leu, or Tyr
<220> FEATURE:
<221> NAME/KEY: MOD_RES
<222> LOCATION: (26)
<223> OTHER INFORMATION: Ile, Val, Ala, or Leu
<220> FEATURE:
<221> NAME/KEY: MOD_RES
<222> LOCATION: (31)
<223> OTHER INFORMATION: Asn, Asp, or Gln
<220> FEATURE:
<223> OTHER INFORMATION: See specification as filed for detailed
      description of substitutions and preferred embodiments

<400> SEQUENCE: 39

Xaa Xaa Asn Thr Ala Thr Xaa Ala Thr Gln Arg Leu Xaa Asn Phe Leu
 1               5                  10                  15

Xaa Xaa Xaa Xaa Xaa Asn Xaa Gly Pro Xaa Leu Pro Pro Thr Xaa Val
             20                  25                  30

Gly Ser Asn Thr Tyr
             35
```